US010244975B2

(12) United States Patent
Wrenn

(10) Patent No.: US 10,244,975 B2
(45) Date of Patent: Apr. 2, 2019

(54) MENTAL HEALTH ASSESSMENT METHOD AND KIOSK-BASED SYSTEM FOR IMPLEMENTATION

(71) Applicant: MOREHOUSE SCHOOL OF MEDICINE, Atlanta, GA (US)

(72) Inventor: Glenda Wrenn, Atlanta, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

(21) Appl. No.: 15/295,489

(22) Filed: Oct. 17, 2016

(65) Prior Publication Data
US 2018/0103885 A1   Apr. 19, 2018

(51) Int. Cl.
| G09B 7/02 | (2006.01) |
| A61B 5/16 | (2006.01) |
| A61B 5/00 | (2006.01) |
| G16H 10/20 | (2018.01) |
| G16H 10/60 | (2018.01) |
| G16H 50/30 | (2018.01) |
| G16H 20/70 | (2018.01) |

(52) U.S. Cl.
CPC .............. *A61B 5/16* (2013.01); *A61B 5/0022* (2013.01); *A61B 5/4088* (2013.01); *A61B 5/742* (2013.01); *A61B 5/746* (2013.01); *G16H 10/20* (2018.01); *G16H 10/60* (2018.01); *G16H 20/70* (2018.01); *G16H 50/30* (2018.01); *A61B 5/6888* (2013.01)

(58) Field of Classification Search
CPC ....................................................... G09B 7/02

USPC ......................................................... 434/236
See application file for complete search history.

(56) References Cited

U.S. PATENT DOCUMENTS

| 6,022,315 A | 2/2000 | Iliff |
| 8,986,014 B2 | 3/2015 | Murray |
| 2011/0112852 A1 | 5/2011 | Ware et al. |
| 2011/0151418 A1 | 6/2011 | Delespaul et al. |
| 2011/0229867 A1* | 9/2011 | Gough ............... G09B 7/02 434/323 |
| 2011/0231208 A1 | 9/2011 | Kaplin |
| 2013/0060580 A1* | 3/2013 | Chapman ........... G06Q 50/22 705/3 |
| 2014/0114680 A1 | 4/2014 | Mills et al. |
| 2015/0324532 A1 | 11/2015 | Jones et al. |

OTHER PUBLICATIONS

International Search Report and Written Opinion of International Patent Application issued in PCT/US2016/057340, dated Jan. 10, 2017.

* cited by examiner

*Primary Examiner* — Thomas Hong
(74) *Attorney, Agent, or Firm* — Ping Wang; Morris, Manning & Martin, LLP

(57) ABSTRACT

A method and system for assessing the mental state or behavioral disorder of a subject is disclosed. The system includes a display, an input device, a processor, a database and matrix for converting the responses to one or more assessment scores. The disclosure also relates to a method for treating a behavioral disorder using the method and a system described herein.

9 Claims, 4 Drawing Sheets

MENTAL HEALTH ASSESSMENT METHOD AND KIOSK-BASED SYSTEM FOR IMPLEMENTATION

FIELD

This disclosure is generally related to systems and methods for assessing health. More specifically, this disclosure is related to systems and methods for assessing or determining a mental state of a subject using a kiosk.

BACKGROUND

The 16th Surgeon General's report on mental health reported that mental health is fundamental and that mental disorders are real health conditions. However, since that report, systems for addressing mental disorders remain challenging and often provide unequal opportunities and unequal outcomes.

One aspect of assessing or determining a mental state of a subject is that health care professionals have a limited time with each subject to collect information and provide medical services and/or guidance. In collecting information, behavioral health and social history are often missed. These are often missed because they are more time-consuming to collect and the answers are often more sensitive. Moreover, research has shown that subjects are more likely to disclose sensitive information to a computer rather than to staff. Subjects also often spend a considerable amount of time in a waiting room to see a health care professional. Having subjects provide behavioral health and social history information while they are waiting would increase the efficiency of health care delivery.

Accordingly, there is a need for systems and methods to collect behavioral health and social history information in a sensitive and effective manner to increase efficiency of health care delivery.

The present application fulfills a need for a system and method for collecting information from a subject for mental health evaluation of the information by healthcare professionals to determine the mental competency of the subject and/or the need for treatment of a subject for a behavioral disorder.

SUMMARY

One aspect of the present application relates to a method for assessment of a mental state of a human subject. The method includes the steps of: prompting the subject with at least one question on a display of a system for assessment of the mental state of the subject; recording at least one response to the at least one question in the system; calculating an assessment score based on the at least one response; determining by at least one health professional, based on the at least one response and/or the assessment score, the mental state of the subject; and incorporating the mental state of the subject into an electronic health record associated with the subject, wherein the at least one response comprises a long-form answer and wherein the system comprises the display, an input device, a processor, a database and a matrix for converting the at least one response to an assessment score.

Another aspect of the present application relates to a method for treating a behavioral disorder in a subject in need thereof. The method comprises the steps of: prompting the subject with at least one question on a display of a system for assessment of a behavioral disorder of the subject, wherein the system comprises the display, an input device, a processor and a database; recording at least one response to the system, wherein the at least one response comprises a long-form answer; analyzing the at least one response by at least one health professional; determining by the at least one health professional, based on the at least one response, the mental state or behavioral disorder of the subject; and incorporating the mental state or behavioral disorder of the subject into an electronic health record associated with the subject. The method further comprises administering to the subject at least one treatment effective for the behavioral disorder. By incorporating the mental state or behavioral state of the subject in an electronic health record, the present application provides a means for alerting authorities concerning potential dangers or risks associated with owning and/or operating firearms, motor vehicles, etc.

In some embodiments, the method further comprises the step of retrieving a medical history of the subject from a database and accepting the at least one attribute from the medical history for the determination of the mental state or behavioral disorder of the subject. In some embodiments, the method further comprises the step of presenting one or more questions about the medical history of the subject and receiving responses to the one or more questions about the medical history of the subject for the determination of the mental state or behavioral disorder of the subject.

In some embodiments, the at least one attribute from the medical history and/or the at least one response to the one or more questions about the medical history triggers an automatic alert for review by the at least one health professional if the at least one attribute from the medical history and/or the at least one response to the one or more questions about the medical history matches an alert event in an alert database.

Still another aspect of the present application relates to a system for assessing the mental state of a subject. The system comprises: a computer-readable memory, the computer-readable memory configured to store computer-executable instructions; an input device configured to receive an input from the subject; and a processor configured to execute the computer-executable instructions, the computer-executable instructions comprising: prompting the subject with at least one question in a system for assessment of mental state on a display; recording at least one response to the at least one assessment, wherein the at least one response comprises a long-form answer; converting the at least one response into at least one assessment score; generating an output comprising the at least one assessment score for assessment of the mental state of the subject by at least one health professional, generating a report of the mental state of the subject based on the assessment by the at least one health professional and incorporating the report into an electronic health record associated with the subject.

In some embodiments, the processor is configured to execute additional computer-executable instructions, including the step of retrieving a medical history of the subject from a database and accepting the at least one attribute from the medical history for the determination of the mental state of the subject. In some embodiments, the processor is configured to execute additional computer-executable instructions, including the step of presenting one or more questions about the medical history of the subject and receiving responses to the one or more questions about the medical history of the subject for the determination of the mental state of the subject.

In some embodiments, the at least one attribute from the medical history and/or the at least one response to the one or more questions about the medical history triggers the system to present an automatic alert for review by the at least one health professional if the at least one attribute from the medical history and/or the at least one response to the one or more questions about the medical history matches an alert event in an alert database.

In some embodiments, the system further comprises a database of alert events, wherein a response to the at least one question, and/or an attribute of a medical history of the subject, triggers the system to present an automatic alert for review by the at least one health professional if the response and/or the attribute matches an alert event in the database.

BRIEF DESCRIPTION OF THE DRAWINGS

The present invention can be better understood by reference to the following drawings, wherein like references numerals represent like elements. The drawings are merely exemplary to illustrate certain features that may be used singularly or in any combination with other features and the present invention should not be limited to the embodiments shown.

DETAILED DESCRIPTION

Figure 1:
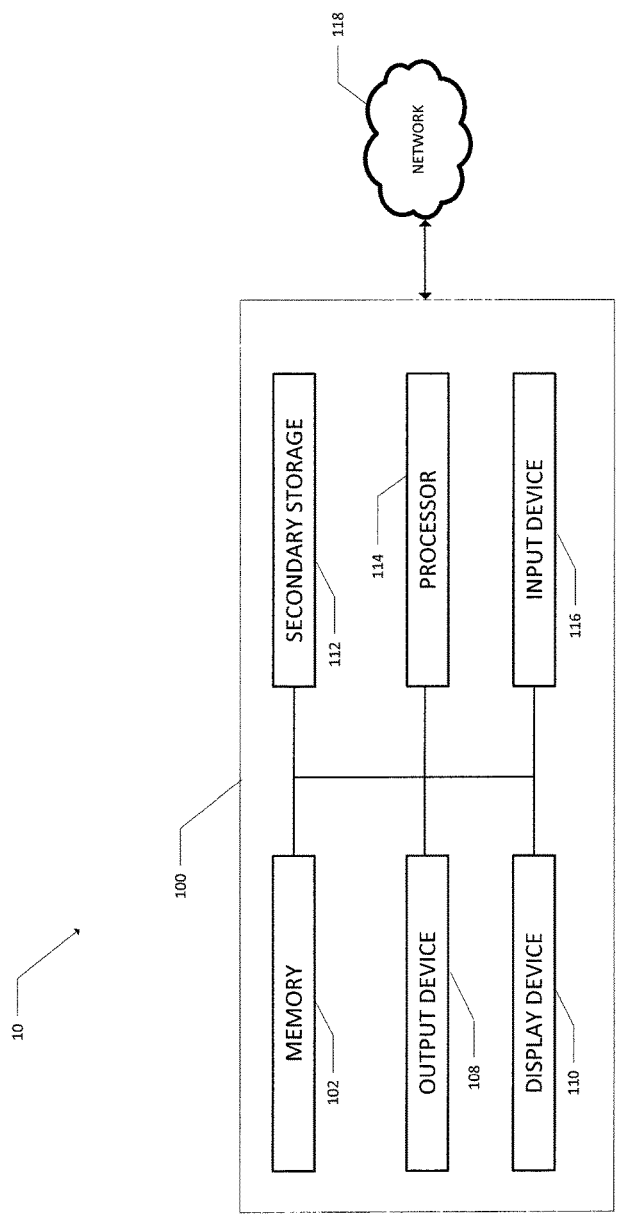
FIG. 1 is a block diagram illustrating exemplary hardware components that may be used for implementing aspects of the system.

The following detailed description is presented to enable any person skilled in the art to make and use the object of this application. For purposes of explanation, specific nomenclature is set forth to provide a thorough understanding of the present application. However, it will be apparent to one skilled in the art that these specific details are not required to practice the subject of this application. Descriptions of specific applications are provided only as representative examples. The present application is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness.

As used herein, the term "mental health" relates to the psychological well-being of a subject. According to the World Health Organization (WHO), mental health includes "subjective well-being, perceived self-efficacy, autonomy, competence, inter-generational dependence, and self-actualization of one's intellectual and emotional potential, among others" (World Health Organization, "World Health Report 2001: Mental Health: New Understanding, New Hope," 2001). The WHO further states that the well-being of an individual is encompassed in the realization of their abilities, coping with normal stresses of life, productive work and contribution to their community.

As used herein, the terms "mental illness," "mental disorder", "behavioral disorder" and "psychiatric disorder" relate to mental health conditions comprising a disorder in the mood, thinking or behavior of a subject. Mental illnesses or behavioral disorders commonly present with cognitive deficits and mood dysregulation. Mental illnesses or behavioral disorders are generally defined by a combination of how a person feels, acts, thinks or perceives. Well established systems for the classification of mental illnesses or behavioral disorders include the International Statistical Classification of Diseases and Related Health Problems, 10th Revision (World Health Organization, tenth revision (2010), the content of which is hereby expressly incorporated by reference in its entirety for all purposes) and the Diagnostic and Statistical Manual of Mental Disorders (fifth edition, DSM-5; American Psychiatric Association, (2013), the content of which is hereby expressly incorporated by reference in its entirety for all purposes). Common examples of mental illnesses or behavioral disorders include schizophrenia, Alzheimer's disease, Huntington's disease, Cushing's disease, Lewy body disease, multiple sclerosis, stroke, addictive disorder, pervasive development disorder, autism, fragile X syndrome, anxiety disorder, mood disorders, Prader-Willi syndrome, bipolar disorder, depressive disorders, behavioral disorders, eating disorders, vascular dementia, mild cognitive impairment, autism, dementia and delirium. The mental illnesses or behavioral disorders also include an organic mental disorder, a mental or behavioral disorder caused by psychoactive substance use, a schizophrenia, schizotypal, or delusional disorder, a mood (affective) disorder, neurotic, stress-related, or somatoform disorder, a behavioral syndrome, an adult personality or behavior disorder, a psychological development disorder, or a child onset behavioral or emotional disorders.

Depressive disorders affect over fifteen percent (15%) of the population. Depression is a mental state of depressed mood characterized by feelings of sadness, despair, and discouragement. Depression includes the normal feelings of "the blues" through dysthymic disorder to major depressive disorder. Dysthymic disorder is a mood disorder characterized by depressed feeling (sad, blue, low), loss of interest or pleasure in usual activities, and at least some of the following: changes in appetite and sleep patterns, lack of energy, low self-esteem, poor concentration or decision-making skills, and feelings of hopelessness. In dysthymic disorders, symptoms have persisted for more than two years but are not severe enough to meet the criteria for major depressive disorder. Major depressive disorder is characterized by major depressive episodes, a period of daily depressed mood or loss of interest or pleasure in almost all activities with some combination of the following symptoms: altered appetite, weight, or sleep patterns, psychomotor agitation or retardation, diminished capacity for thinking, concentration, or decisiveness, lack of energy and fatigue, feelings of worthlessness, self-reproach, or guilt, frequent thoughts of death or suicide, plans or attempts to commit the latter (Diagnostic and Statistical Manual of Mental Disorders, 4th ed., American Psychiatric Association, Washington D.C., 1994).

As used herein, the term "behavioral disorder" relates to a disorder characterized by displayed behaviors over a long period of time which significantly deviate from socially acceptable norms for a person's age and situation. Exemplary behavioral disorders include, but are not limited to, anxiety disorders (including post-traumatic stress disorder (PTSD), obsessive-compulsive disorder (OCD), generalized anxiety disorder, and panic disorder), disruptive disorders, dissociative disorders, emotional disorders, pervasive developmental disorders and substance abuse. In some embodiments, the behavior disorder includes, or is caused by, a mental disorder or a behavioral disorder.

As used herein, the term "mental competency" relates to the ability of a subject to act in the circumstances, including the ability to perform a task, job or occupation, or to reason or make decisions. A subject's mental competency can be assessed by the present method and system to determine, for example, whether the subject should be allowed to purchase a firearm, or whether the subject can perform a job function, such as a pilot. Accordingly, a system of the present application can be made available at point of service locations including, but not limited to, retail establishments, medical facilities or offices, or employment agencies/offices.

As used herein, the term "assessment" relates to determination of the mental state of a subject, determination of changes in the mental state of a subject, determination/diagnosis of a mental illness in a subject or determination/diagnosis of changes in a mental illness in a subject.

As used herein, the term "long-form answer" relates to an answer to a question that is more than a single word answer such as, yes, no, maybe, true or false.

As used herein, the term "subject" relates to a human individual or subject in need of analysis of a mental state for mental competency or diagnostic purposes.

As used herein, the terms "health professional" or "healthcare provider" relate to an individual who provides preventive, curative, promotional or rehabilitative health care services in a systematic way to people, families or communities. Health professionals include, but are not limited to, physicians, psychiatrists, psychologists, pharmacists, physician assistants, nurses, nurse practitioners, advanced practice registered nurses, surgeons, surgeon's assistant, therapists, chiropractors, clinical officers, social workers, operating department practitioners, and a wide variety of other human resources trained to provide some type of health care service.

As used herein, the terms "physician" or "medical doctor" relate to a professional who practices medicine, and is concerned with promoting, maintaining, or restoring health through the study, diagnosis, and treatment of disease, injury, and other physical and mental impairments. A physician may include, but is not limited to, a primary care physician of a subject; a staff physician in a hospital, nursing home, clinic or other medical care facility; a physician who is a member of a medical group; a general practitioner; a Doctor of Osteopathic Medicine or a family physician. In some embodiments, the term "physician" does not include a psychiatrist or a psychologist.

As used herein, the term "mental health professional" relates to a health care practitioner or community services provider who offers services for the purpose of improving an individual's mental health or to treat mental illness. A mental health professional includes, but is not limited to, a psychiatrist and a psychologist.

Method for Assessment of a Mental State of a Human Subject

One aspect of the present application relates to a method for assessment of a mental state of a human subject. The method comprises the steps of: prompting the subject with at least one question on a display of a system for assessment of the mental state of the subject; recording at least one response to the at least one question in the system; calculating an assessment score based on the at least one response; determining by at least one health professional, based on the at least one response and/or the assessment score, the mental state of the subject; and incorporating the mental state of the subject into an electronic health record associated with the subject, wherein the at least one response comprises a long-form answer and wherein the system comprises the display, an input device, a processor, a database and a matrix for converting the at least one response to an assessment score.

In some embodiments, the method further comprises the step of retrieving a medical history of the subject from a database and accepting the at least one attribute from the medical history for the determination of the mental state of the subject. In some embodiments, the method further comprises the step of presenting one or more questions about the medical history of the subject and receiving responses to the one or more questions about the medical history of the subject for the determination of the mental state of the subject.

In some embodiments, the at least one attribute from the medical history and/or the at least one response to the one or more questions about the medical history triggers an automatic alert for review by the at least one health professional if the at least one attribute from the medical history and/or the at least one response to the one or more questions about the medical history matches an alert event in an alert database.

In some embodiments, the method comprises analyzing the at least one response by two health professionals. In some further embodiments, the at least one health professional is a mental health professional. In some still further embodiments, the mental health professional is a psychiatrist. In other further embodiments, the at least one health professional is a physician. In some yet further embodiments, the two health professionals are a physician and a mental health professional.

In some embodiments, the assessment of a mental state includes the determination or diagnosis of a mental illness or a behavioral disorder.

In some embodiments, the mental illness or a behavioral disorder is caused or related to a disorder of the central nervous system. As used herein, the terms "disorder of the central nervous system", "central nervous system disorder", "CNS disorder", and the like refer to a disorder affecting either the spinal cord (e.g., a myelopathy) or brain (e.g., an encephalopathy) of a subject, which commonly presents with neurological and/or psychiatric symptoms. CNS disorders include many neurodegenerative diseases (e.g., Huntington's disease, Amyotrophic lateral sclerosis (ALS), hereditary spastic hemiplegia, primary lateral sclerosis, spinal muscular atrophy, Kennedy's disease, Alzheimer's disease, ataxias, Huntington's disease, Lewy body disease, a polyglutamine repeat disease, and Parkinson's disease) and behavioral disorders (e.g., mood disorders, schizophrenias, and autism). Non-limiting examples of ataxia include Friedreich's ataxia and the spinocerebellar ataxias. Specifically for this application, CNS disorders do not include disorders resulting from acute viral and bacterial infections.

Non-limiting examples of CNS disorders include neurodegenerative disorders of the central nervous system, systemic atrophies primarily affecting the central nervous system, extrapyramidal and movement disorders, demyelinating disorders of the central nervous system, episodic or paroxysmal disorders of the central nervous system, paralytic syndromes of the central nervous system, nerve, nerve root, or plexus disorders of the central nervous system, organic mental disorders, mental or behavioral disorders caused by psychoactive substance use, schizophrenic, schizotypal, or delusional disorders, mood (affective) disorders, neurotic, stress-related, or somatoform disorders, behavioral syndromes, adult personality or behavior disorders, psychological development disorders, and child onset behavioral or emotional disorders. (Diagnostic and Statistical Manual of Mental Disorders, 5th Edition (DSM-5, 2013); The World Health Organization, The International Classification of Diseases, 10th revision (ICD-10), Chapter V.

In some embodiments, the mental illness or behavioral disorder is caused by neurodegenerative CNS disorders. Neurodegenerative CNS disorders are typically characterized by progressive dysfunction and/or cell death in the central nervous system. The hallmark of many neurodegenerative CNS disorders is the accumulation of misfolded proteins, such as beta-amyloid, tau, alpha-synuclein, and TDP-43, both intracellularly and extracellularly. Many neurodegenerative diseases are also associated with gross mitochondrial dysfunction. Common examples of neurodegenerative CNS disorders include Alzheimer's disease (AD), Parkinson's disease (PD), Huntington's disease, and Amyotrophic lateral sclerosis (ALS), a circumscribed brain atrophy (e.g., Pick's disease); senile degeneration of brain; a degeneration of nervous system due to alcohol; grey-matter degeneration (e.g., Alpers' disease); Lewy body dementia, subacute necrotizing encephalopathy (e.g., Leigh's disease); and subacute combined degeneration of spinal cord.

In some embodiments, the mental illness or behavioral disorder is caused by CNS disorders selected from the group consisting of a systemic atrophy primarily affecting the central nervous system, an extrapyramidal and movement disorder, a neurodegenerative disorder of the central nervous system, a demyelinating disorder of the central nervous system, an episodic or paroxysmal disorder of the central nervous system, a paralytic syndrome of the central nervous system, a nerve, nerve root, or plexus disorder of the central nervous system.

Non-limiting examples of systemic atrophies that primarily affect the central nervous system include: Huntington's disease; hereditary ataxias (e.g., congenital non-progressive ataxia, early-onset cerebellar ataxias—such as early-onset cerebellar ataxia with essential tremor, Hunt's ataxia, early-onset cerebellar ataxia with retained tendon reflexes, Friedreich's ataxia, and X-linked recessive spinocerebellar ataxia—late-onset cerebellar ataxia, ataxia telangiectasia (Louis-Bar syndrome), or hereditary spastic paraplegia); a spinal muscular atrophy or related disorder thereof (e.g., Werdnig-Hoffman disease (Type 1), progressive bulbar palsy of childhood (Fazio-Londe syndrome), Kugelberg-Welander disease (Type 3), or a motor neuron disease—such as familial motor neuron disease, amyotrophic lateral sclerosis (ALS), primary lateral sclerosis, progressive bulbar palsy, and progressive spinal muscular atrophy); paraneoplastic neuromyopathy and neuropathy; systemic atrophy primarily affecting the central nervous system in neoplastic disease; paraneoplastic limbic encephalopathy; and systemic atrophy primarily affecting the central nervous system in myxedema.

In some embodiments, the mental illnesses or behavioral disorders are caused by the CNS disorder selected from the group consisting of Alzheimer's disease, Parkinson's disease, multiple sclerosis, amyotrophic lateral sclerosis (ALS), Huntington's disease, cerebral palsy, bipolar disorder, schizophrenia, Pediatric Autoimmune Neuropsychiatric Disorders Associated with Streptococcal infections (PANDAS), or Pediatric acute-onset neuropyschiatric syndrome (PANS).

In some embodiments, the mental illness or behavioral disorder is caused by an extrapyramidal and movement disorder. Non-limiting examples of extrapyramidal and movement disorders that affect the central nervous system include: Parkinson's disease; a secondary parkinsonism (e.g., malignant neuroleptic syndrome or postencephalitic parkinsonism); a degenerative disease of the basal ganglia (e.g., Hallervorden-Spatz disease, progressive supranuclear ophthalmoplegia (Steele-Richardson-Olszewski disease), or striatonigral degeneration), a dystonia (e.g., drug-induced dystonia, idiopathic familial dystonia, idiopathic non-familial dystonia, spasmodic torticollis, idiopathic orofacial dystonia—such as orofacial dyskinesia—or blepharospasm); an essential tremor; a drug-induced tremor, myoclonus, drug-induced chorea, drug-induced tics; restless legs syndrome; and stiff-man syndrome.

In some embodiments, the mental illness is dementia. In certain embodiments, the dementia is a cortical dementia (associated, for example, with Alzheimer's) arising from a disorder affecting the cerebral cortex. In certain embodiments, the dementia is a subcortical dementia (associated, for example, with Parkinson's disease and Huntington's disease) resulting from dysfunction in the parts of the brain that are beneath the cortex. In certain embodiments, the dementia is a side effect of drug administration. In specific embodiments, the dementia is a side effect of the administration of a chemotherapeutic agent. In specific embodiments, the dementia is a result of undergoing cardiac bypass. In specific embodiments, the dementia is a result of a vascular disorder (e.g., myocardial infarction, stroke, high blood pressure). In specific embodiments, the dementia is a result of depression.

In some embodiments, the mental illness or behavioral disorder is caused by a demyelinating disorder of the central nervous system. Non-limiting examples of demyelinating disorders that affect the central nervous system include: multiple sclerosis; an acute disseminated demyelination disorder (e.g., neuromyelitis optica (Devic's syndrome) or acute and subacute hemorrhagic leukoencephalitis (Hurst's disease)); diffuse sclerosis; central demyelination of corpus callosum; central pontine myelinolysis; acute transverse myelitis in demyelinating disease of central nervous system; subacute necrotizing myelitis; and concentric sclerosis (Balo disease).

In some embodiments, the mental illness or behavioral disorder is caused by an episodic or paroxysmal disorder of the central nervous system. Non-limiting examples of episodic and paroxysmal disorders that affect the central nervous system include: epilepsy (e.g., localization-related (focal)(partial) idiopathic epilepsy and epileptic syndromes with seizures of localized onset, localization-related (focal)(partial) symptomatic epilepsy and epileptic syndromes with simple partial seizures; localization-related (focal)(partial) symptomatic epilepsy and epileptic syndromes with complex partial seizures; a benign epileptic syndrome—such as myoclonic epilepsy in infancy and neonatal convulsions (familial)—childhood absence epilepsy (e.g., pyknolepsy), epilepsy with grand mal seizures on awakening, a juvenile epilepsy—such as absence epilepsy or myoclonic epilepsy (impulsive petit mal)—a nonspecific epileptic seizure—such as an atonic, clonic, myoclonic, tonic, or tonic-clonic epileptic seizure, epilepsy with myoclonic absences or myoclonic-astatic seizures, infantile spasms, Lennox-Gastaut syndrome, Salaam attacks, symptomatic early myoclonic encephalopathy, West's syndrome, epilepsia partialis continua (Kozhevnikov epilepsy), grand mal seizures, or petit mal); headaches (e.g., a migraine—such as a migraine without aura (common migraine), a migraine with aura (classical migraine), status migrainosus, and complicated migraine—cluster headache syndrome, a vascular headache, a tension-type headache, a chronic post-traumatic headache, or a drug-induced headache); a cerebrovascular episodic or paroxysmal disorder (e.g., a transient cerebral ischaemic attacks or related syndrome—such as vertebrobasilar artery syndrome, carotid artery syndrome (hemispheric), a multiple and bilateral precerebral artery syndrome, amaurosis fugax, and transient global amnesia—a vascular syndrome of the brain—such as middle cerebral artery syndrome, anterior cerebral artery syndrome, posterior cerebral artery syndrome, a brain stem stroke syndrome (e.g., Benedikt syndrome, Claude syndrome, Foville syndrome, Millard-Gubler syndrome, Wallenberg syndrome, or Weber syndrome), cerebellar stroke syndrome, pure motor lacunar syndrome, pure sensory lacunar syndrome, or a lacunar syndromes); and a sleep disorder (e.g., insomnia, hyperinsomnia, a disruption in circadian rhythm, sleep apnea, narcolepsy, or cataplexy).

In some embodiments, the mental illness or behavioral disorder is caused by a CNS disorder is a paralytic syndrome of the central nervous system. Non-limiting examples of paralytic syndromes that affect the central nervous system include: a cerebral palsy (e.g., spastic quadriplegic cerebral palsy, spastic diplegic cerebral palsy, spastic hemiplegic cerebral palsy, dyskinetic cerebral palsy, or ataxic cerebral palsy); a hemiplegia (e.g., flaccid hemiplegia or spastic hemiplegia); a paraplegia or tetraplegia (e.g., flaccid paraplegia, spastic paraplegia, paralysis of both lower limbs, lower paraplegia, flaccid tetraplegia, spastic tetraplegia, or quadriplegia); diplegia of upper limbs; monoplegia of a lower limb, monoplegia of an upper limb; cauda equina syndrome; and Todd's paralysis (postepileptic).

In some embodiments, the mental illness or behavioral disorder is caused by an otherwise classified disorder of the central nervous system. Non-limiting examples of these disorders include: hydrocephalus; a toxic encephalopathy, a cerebral cyst; anoxic brain damage; benign intracranial hypertension; postviral fatigue syndrome; an encephalopathy; compression of brain; cerebral oedema; Reye's syndrome; postradiation encephalopathy; traumatic brain injury; syringomyelia; syringobulbia; a vascular myelopathy; spinal cord compression; myelopathy; a cerebrospinal fluid leak; a disorder of the meninges (e.g., cerebral or spinal meningeal adhesion); and a post-procedural disorder of nervous system (e.g., cerebrospinal fluid leak from spinal puncture, an adverse reaction to a spinal or lumbar puncture, or intracranial hypotension following ventricular shunting).

In some embodiments, the mental illness is an organic mental disorder. Non-limiting examples of organic mental disorders that affect the central nervous system include: dementia (e.g., dementia associated with Alzheimer's disease, Pick's disease, Creutzfeldt-Jakob disease, Huntington's disease, Parkinson's disease, or human immunodeficiency virus (HIV) disease, or vascular dementia—such as multi-infarct dementia); organic amnesic syndrome not induced by alcohol and other psychoactive substances); delirium not induced by alcohol and other psychoactive substances; a mental disorder due to brain damage and dysfunction and to physical disease (e.g., organic hallucinosis, organic catatonic disorder, organic delusional (schizophrenia-like) disorder, organic mood (affective) disorder, organic anxiety disorder, organic dissociative disorder; organic emotionally labile (asthenic) disorder; a mild cognitive disorder, or organic brain syndrome); and a personality and behavioral disorders due to brain disease, damage and dysfunction (e.g., organic personality disorder, postencephalitic syndrome, or postconcussional syndrome).

In some embodiments, the mental illness or behavioral disorder is a mental or behavioral disorder caused by psychoactive substance use. Non-limiting examples of mental or behavioral disorders caused by psychoactive substance use that affect the central nervous system include: acute intoxication (e.g., from alcohol, opioid, cannabis, benzodiazepine, or cocaine use); a dependence syndrome (e.g., from alcohol, opioid, cannabis, benzodiazepine, cocaine, or nicotine addiction); a withdrawal syndrome (e.g., an alcohol or benzodiazepine withdrawal syndrome); delirium tremens; and a psychotic disorder (e.g., alcoholic hallucinosis or stimulant psychosis); an amnesic syndrome (e.g., Korsakoff s syndrome); a residual and late-onset psychotic disorder (e.g., posthallucinogen perception disorder).

In some embodiments, the mental illness or behavioral disorder is an autism spectrum disorder. In certain embodiments, the CNS disorder is autism, Asperger syndrome, pervasive developmental disorder not otherwise specified (PDD-NOS), childhood disintegrative disorder, or Rett syndrome.

In some embodiments, the mental illness or behavioral disorder is a schizophrenia, schizotypal, or delusional disorder. Non-limiting examples of schizophrenia, schizotypal, and delusional disorders that affect the central nervous system include: schizophrenia (e.g., paranoid schizophrenia, hebephrenic schizophrenia (disorganized schizophrenia), catatonic schizophrenia, undifferentiated schizophrenia, post-schizophrenic depression, residual schizophrenia, simple schizophrenia, cenesthopathic schizophrenia, schizophreniform disorder, or schizophreniform psychosis); schizotypal disorder; a persistent delusional disorder (e.g., delusional disorder, delusional dysmorphophobia, involutional paranoid state, or paranoia querulans); an acute or transient psychotic disorder (e.g., acute polymorphic psychotic disorder without symptoms of schizophrenia, acute polymorphic psychotic disorder with symptoms of schizophrenia, or acute schizophrenia-like psychotic disorder); an induced delusional disorder (e.g., folie a deux, induced paranoid disorder, or induced psychotic disorder); a schizoaffective disorder (e.g., manic type, depressive type, or mixed type schizoaffective disorder); and chronic hallucinatory psychosis.

In some embodiments, the mental illness or behavioral disorder is a mood (affective) disorder. Non-limiting examples of mood (affective) disorders that affect the central nervous system include: a manic episode (e.g., hypomania, mania without psychotic symptoms, or mania with psychotic symptoms); a bipolar affective disorder (e.g., bipolar affective disorder—current episode hypomanic, bipolar affective disorder—current episode manic without psychotic symptoms, bipolar affective disorder—current episode manic with psychotic symptoms, bipolar affective disorder—current episode mild or moderate depression, bipolar affective disorder—current episode severe depression without psychotic symptoms, bipolar affective disorder—current episode severe depression with psychotic symptoms, bipolar affective disorder—current episode mixed, bipolar affective disorder—currently in remission, bipolar II disorder, or recurrent manic episodes); a depressive episode (e.g., mild depressive episode, moderate depressive episode, severe depressive episode without psychotic symptoms, severe depressive episode with psychotic symptoms, atypical depression, or single episodes of "masked" depression); a recurrent depressive disorder (e.g., recurrent depressive disorder—current episode mild, recurrent depressive disorder—current episode moderate, recurrent depressive disorder—current episode severe without psychotic symptoms, recurrent depressive disorder—current episode severe with psychotic symptoms, or recurrent depressive disorder—currently in remission); a persistent mood (affective) disorder (e.g., cyclothymia or dysthymia); mixed affective episode; and recurrent brief depressive episodes.

In some embodiments, the mental illness or behavioral disorder is a neurotic, stress-related, or somatoform disorder. Non-limiting examples of neurotic, stress-related, or somatoform disorders that affect the central nervous system include: a phobic anxiety disorder (e.g., agoraphobia, anthropophobia, social neurosis, acrophobia, animal phobias, claustrophobia, or simple phobia); an otherwise categorized anxiety disorder (e.g., panic disorder (episodic paroxysmal anxiety) or generalized anxiety disorder); obsessive-compulsive disorder; an adjustment disorder (e.g., acute stress reaction; post-traumatic stress disorder, or adjustment disorder); a dissociative (conversion) disorder (e.g., dissociative amnesia, dissociative fugue, dissociative stupor; trance disorder, possession disorder, dissociative motor disorder, dissociative convulsions, dissociative anaesthesia and sensory loss, mixed dissociative (conversion) disorder, Ganser's syndrome, or multiple personality disorder); a somatoform disorder (e.g., Briquet's disorder, multiple psychosomatic disorder, a hypochondriacal disorder—such as body dysmorphic disorder, dysmorphophobia (nondelusional), hypochondriacal neurosis, hypochondriasis, and nosophobia—a somatoform autonomic dysfunction—such as cardiac neurosis, Da Costa's syndrome, gastric neurosis, and neurocirculatory asthenia—or psychalgia); neurasthenia; depersonalization-derealization syndrome; Dhat syndrome, occupational neurosis (e.g., writer's cramp); psychasthenia; psychasthenic neurosis; and psychogenic syncope.

In some embodiments, the mental illness or behavioral disorder is a behavioral syndrome associated with physiological disturbances or physical factors. Non-limiting examples of behavioral syndromes associated with physiological disturbances or physical factors that affect the central nervous system include: an eating disorder (e.g., anorexia nervos, atypical anorexia nervosa, bulimia nervosa, atypical bulimia nervosa, overeating associated with other psychological disturbances, vomiting associated with other psychological disturbances, or pica in adults); a nonorganic sleep disorder (e.g., nonorganic insomnia, nonorganic hypersomnia, nonorganic disorder of the sleep-wake schedule, sleepwalking (somnambulism), sleep terrors (night terrors), or nightmares); a sexual dysfunction not caused by organic disorder or disease; a mental or behavioral disorder associated with the puerperium (e.g., postnatal depression, postpartum depression, or puerperal psychosis); and abuse of non-dependence-producing substances.

In some embodiments, the mental illness or behavioral disorder is an adult personality or behavior disorder. Non-limiting examples of adult personality and behavior disorders that affect the central nervous system include: a specific personality disorder (e.g., paranoid personality disorder, schizoid personality disorder, a dissocial personality disorder—such as antisocial personality disorder—an emotionally unstable personality disorder—such as borderline personality disorder—histrionic personality disorder, an anankastic personality disorder—such as obsessive-compulsive personality disorder, anxious (avoidant) personality disorder, dependent personality disorder, eccentric personality disorder, haltlose personality disorder, immature personality disorder, narcissistic personality disorder, passive-aggressive personality disorder, or psychoneurotic personality disorder); mixed personality disorder; a habit or impulse disorder (e.g., pathological gambling, pathological fire-setting (pyromania), pathological stealing (kleptomania), or trichotillomania); and Munchausen syndrome.

In some embodiments, the mental illness or behavioral disorder is a psychological development disorder. Non-limiting examples of psychological development disorders that affect the central nervous system include: a developmental disorder of speech or language (e.g., specific speech articulation disorder, expressive language disorder, receptive language disorder (receptive aphasia), acquired aphasia with epilepsy (Landau-Kleffner disorder), or lisping); a developmental disorder of scholastic skills (e.g., a specific reading disorder—such as developmental dyslexia—specific spelling disorder, a specific disorder of arithmetical skills—such as developmental acalculia and Gerstmann syndrome—or a mixed disorder of scholastic skills); a developmental disorder of motor function (e.g., developmental dyspraxia); a mixed specific developmental disorder; and a pervasive developmental disorder (e.g., childhood autism, atypical autism, Rett's syndrome, overactive disorder associated with mental retardation and stereotyped movements, or Asperger's syndrome).

In some embodiments, the mental illness or behavioral disorder is a behavioral or emotional disorder with onset usually occurring in childhood and adolescence. Non-limiting examples of behavioral or emotional disorders with onset usually occurring in childhood and adolescence that affect the central nervous system include: a hyperkinetic disorder (e.g., a disturbance of activity and attention—such as attention-deficit hyperactivity disorder and attention deficit syndrome with hyperactivity—or hyperkinetic conduct disorder); a conduct disorder (e.g., conduct disorder confined to the family context, unsocialized conduct disorder, socialized conduct disorder, or oppositional defiant disorder); a mixed disorder of conduct or emotions (e.g., depressive conduct disorder); an emotional disorder with onset specific to childhood (e.g., separation anxiety disorder of childhood, phobic anxiety disorder of childhood, social anxiety disorder of childhood, sibling rivalry disorder, identity disorder, or overanxious disorder); a disorder of social functioning with onset specific to childhood and adolescence (e.g., elective mutism, reactive attachment disorder of childhood, or disinhibited attachment disorder of childhood); a tic disorder (e.g., transient tic disorder, chronic motor or vocal tic disorder, or combined vocal and multiple motor tic disorder (de la Tourette)); and an otherwise classified behavioral or emotional disorder with onset usually occurring in childhood and adolescence (e.g., nonorganic enuresis, non-organic encopresis, feeding disorder of infancy and childhood, pica of infancy and childhood, stereotyped movement disorders, stuttering (stammering), cluttering, attention deficit disorder without hyperactivity, Pediatric Autoimmune Neuropsychiatric Disorders Associated with Streptococcal infections (PANDAS), or Pediatric acute-onset neuropyschiatric syndrome (PANS)).

In some embodiments, the at least one response prompts the system to present at least one additional question related to the at least one response. In related embodiments, the at least one response prompts the system to present at least one set of additional questions related to the at least one response. In some further embodiments, a set of additional questions comprises at least 2, 3, 4, 5, 6, 7, 8, 9, 10, 11, 12, 13, 14, 15, 16, 17, 18, 19 or 20 questions.

In other embodiments, the at least one response or responses of the subject to the at least one additional question or to the at least one set of additional questions prompts the system to present at least one additional question related to a different facet of the mental health of the subject. In related embodiments, the at least one response or responses of the subject to the at least one additional question or to the at least one set of additional questions prompts the system to present at least one set of additional questions related to a different facet of the mental health of the subject. In some further embodiments, a set of additional questions comprises at least 2, 3, 4, 5, 6, 7, 8, 9, 10, 11, 12, 13, 14, 15, 16, 17, 18, 19 or 20 questions. In other related embodiments, the system present the subject with questions or sets of questions related to at least 2, 3, 4, 5, 6, 7, 8, 9, 10, 11, 12, 13, 14, 15, 16, 17, 18, 19 or 20 facets of mental health.

In some embodiments, the method comprises analyzing the at least one response by two health professionals. In some further embodiments, the at least one health professional is a mental health professional. In some still further embodiments, the mental health professional is a psychiatrist. In other further embodiments, the at least one health professional is a physician, who is in some embodiments the primary care physician of the subject. In some yet further embodiments, the two health professionals are a physician and a mental health professional.

In some embodiments, the method further comprises the step of retrieving a medical history of the subject from a database and accepting the at least one attribute from the medical history for the determination of the mental state of the subject. In some embodiments, the method further comprises the step of presenting one or more questions about the medical history of the subject and receiving responses to the one or more questions about the medical history of the subject for the determination of the mental state or behavioral disorder of the subject.

Attributes from the medical history include a list of previous illnesses, symptoms, medicines, treatments, health risk factors, operations, and/or doctor visits for the subject. In some embodiments, the medical history includes life history and/or social history characteristics such as smoking, drinking, drug use, sexual history, exercise history, eating history, nutraceutical history, or the like. In some embodiments, the medical history includes a family medical history. A family medical history may include a list of previous illnesses, symptoms, medicines, treatments, health risk factors, operations, and/or doctor visits associated with family members related to the subject.

In some embodiments, the at least one attribute includes mental attributes of the subject. A mental attribute may include an attribute that may be related to and/or associated with basic mental function and/or high-level brain function. Some examples of a mental attribute may include an indication of learning disability, cognitive disability, measurements of brain activity, for example using functional MRI or near infra-red technology, and/or measurements of mental development.

In some embodiments, the at least one attribute includes descriptions of mental symptoms of the subject. A mental symptom may include a manifestation, sign, and/or an indication of the presence of a disease and/or some other mental disorder and/or abnormality. Some examples of a mental symptom may include lack of attention, indication of stress, hyperactivity, nervousness, and/or lack of responsiveness.

In some embodiments, the at least one attribute includes indication of anxiety, an appearance, a behavior, depression, fear, inattention, a mood disturbance, a phobia, or a psychological test result. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a low level of energy, and/or a lack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/compulsive characteristics. In some instances, mental indication accepter module 636 may include a computer processor.

In some embodiments, the at least one attribute includes at least one measurement associated with at least one of brain activity, cardiac activity, vascular activity, peripheral neural signals, hemodynamic activity, or metabolic activity. Brain activity may include the electrical activity of the brain, such as that measured by EEG, MEG, or the like. Other brain activity measurements may include functional MM imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, mental activity accepter module 638 may include a computer processor.

In some embodiments, the at least one attribute includes measurement of at least one brain activity surrogate marker. Brain activity surrogate markers may include indicators of attention, approval, disapproval, recognition, cognition, memory, trust, or the like in response to a stimulus, other than measurement of brain activity associated with the stimulus. Some examples of surrogate markers may include a skin response to a stimulus; a face pattern indicative of approval, disapproval, or emotional state; eye movements or pupil movements indicating visual attention to an object; voice stress patterns indicative of a mental state, or the like. Surrogate markers may be used in conjunction with brain activity measurements for higher confidence in a predictive or interpretational outcome. For example, brain activation of the caudate nucleus in combination with calm voice patterns may increase confidence in a predictor of trust between a subject and a stimulus. Additional discussion regarding surrogate markers may be found in Cohn, J. N., Introduction to Surrogate Markers, CIRCULATION 109: IV20-21, American Heart Association, (2004), which is incorporated herein by reference.

In some embodiments, the at least one attribute includes measurement of iris dilation or constriction, gaze tracking, skin response, or voice response. In some embodiments, the medical history includes measurement of changes in the movement of an individual's iris (with corresponding changes in the size of the pupil) before, during, and/or after administration of a bioactive agent and/or an artificial sensory experience. Such measurements of physiologic activity that indicate brain activity and/or mental state may be carried out at a time that is proximate to administration of a bioactive agent and/or an artificial sensory experience.

In some embodiments, the at least one attribute includes measurement of skin response of the subject. Brain activity may be determined by detection of a skin response associated with a stimulus. One skin response that may correlate with mental state and/or brain activity is galvanic skin response (GSR), also known as electrodermal response (EDR), psychogalvanic reflex (PGR), or skin conductance response (SCR). This is a change in the electrical resistance of the skin. There is a relationship between sympathetic nerve activity and emotional arousal, although one may not be able to identify the specific emotion being elicited. The GSR is highly sensitive to emotions in some people. Fear, anger, startle response, orienting response, and sexual feelings are all among the emotions which may produce similar GSR responses. GSR is typically measured using electrodes to measure skin electrical signals. For example, an Ultimate Game study measured skin-conductance responses as a surrogate marker or autonomic index for affective state, and found higher skin conductance activity for unfair offers, and as with insular activation in the brain, this measure discriminated between acceptances and rejections of these offers. See Sanfey, "Social Decision-Making: Insights from Game Theory and Neuroscience," Science, vol. 318, pp. 598-601 (26 Oct. 2007), which is incorporated herein by reference. Other skin responses may include flushing, blushing, goose bumps, sweating, or the like.

In some embodiments, the at least one attribute includes measurement of voice response. Voice response may include speech captured by a microphone during presentation of a characteristic. Speech or voice can be measured, for example, by examining voice, song, and/or other vocal utterances of a subject before, during, and/or after administration of a bioactive agent and/or an artificial sensory experience to an individual. Such measurements may include, for example, as discussed above, layered voice analysis, voice stress analysis, or the like.

In some embodiments, the at least one attribute includes personal identification data, physical characteristics data, health profile data, family health history data, drug and vitamin/mineral supplement data, health baseline data, diet and nutritional data, environmental exposure data, and behavioral data.

The personal identification data comprises essential personal information that facilitates the identification of an individual and the establishment of core demographic characteristics. For example, the personal identification data includes name, address, residence history, age, gender, race, ethnicity, education, sexual preference, martial status, living arrangements, marital history, children, occupation, work history, home and work environments, travel history, military service history, genealogy, relationships, recreational activities and the like. Sensitive information, such as name and street address, may be segregated and coded for privacy and security.

The physical characteristics data includes height, weight, body fat ratio, body symmetry and dimensions, skin shade and texture, eye color, hair growth/color and texture, strength symmetry, endurance, coordination, posture, gait, nail growth and features, feet size, physical peculiarities, physical deformities, growths, blemishes, teeth and gums, flexibility, and the like. These characteristics are useful in establishing the subscriber's physical uniqueness as well as their membership in population groups that share certain characteristics.

The health profile data comprises a broad array of information pertaining to the subscriber's psychological and physiological characteristics and condition, medical history data, hazardous and toxic material exposure data, allergies data, disabilities, reproductive history, depression data, family (genealogy) health history data stress level data, mental condition data, current health conditions data, physical sensitivities and pain data, activity level and physical fitness data, illnesses history data, history of injuries data, chronic conditions data, visual acuity data, night vision data, hearing acuity data, reaction time data and the like. The health profile data also incorporates the results of quantitative tests including blood chemistry tests, breath analysis (i.e., laser absorption spectroscopy), medical imaging (i.e., x-rays, magnetic resonance imaging, lithotripsy, computed tomography, fluorescence spectroscopy, ultrasounds, thermographs, and others), photographic imaging, and other psychological, physical, and physiological tests.

The family health history addresses the health conditions and unique characteristics of the subject's living and deceased blood relatives. The family health history data is comprised of personal description data, physical description data, physical characteristics, demographic data, occupational data, disabilities, behaviors, health and medical histories, and the like. The family history data collection includes names, birthdates, place of birth, number of children (including genders and birthdates), places of residency, health histories, ages at death, height, weight, physical and health peculiarities, chronic conditions, sensitivities/allergies, disease history, cause of death, health conditions at time of death, history of injuries, deformities, visual acuity, hearing acuity, mental condition and acuity, disabilities, occupations/professions, medication history (including diagnosis, treatments, test results, evaluations, and the like), reproductive histories, alcohol and drug usage, blood types, and other psychological, physical, physiological and behavioral details that would be useful in the identification of genetic characteristics and predispositions.

The drug and vitamin/mineral supplement data comprises a detailed history of prescription and non-prescription drugs, vitamin supplements, herbs, and mineral supplement usages. Included in the history may be the item description, dosage, frequency taken, date started, reason for taking, date stopped, reason for stopping, and observed effects, side effects, reactions, and the like.

The health baseline data may, in part, be derived from information compiled in previous databases including, the personal identification data, physical characteristics data and health profile data. Certain key psychological characteristics (i.e., depression, confusion, neurosis and other like mental conditions or mental cognitive peculiarities), physical characteristics (i.e., height, weight, body fat ratio, posture, flexibility, mobility, hair growth, hair color, skin color/tone, eye color and the like), physiological characteristics (i.e., visual performance, hearing performance, blood pressure, heart rate, repertory rate, heart rhythm, blood chemistry, and other major organ system performance characteristics), and medical conditions may be recorded and updated over a period of time. The resulting database will depict each characteristic separately and their respective performance values.

In some cases, the data may be subject to a patterns-analysis, which identifies repetitive fluctuations in order to establish predictable patterns, ranges of fluctuation and rate of change. Where possible, certain pattern fluctuations are linked to predictable cycles, such as, time-of-day, seasons, and biological cycles. In addition, the subscriber's physical, psychological, physiological and behavioral characteristics (including patterns) may be assessed relative to authoritative standards and norms of similar population groups. The resulting compilation of data forms a baseline or reference-point to which new data, representing the latest health condition of the subscriber for comparison. The comparison provides a basis for determining whether the new data is consistent with or deviates from the baseline. The deviations may be positive (improvements in a condition), negative (evidence of deterioration), or they may be evidence of a new condition or abnormality.

The diet and nutritional data (also referred to as diet and nutritional profile) systematically records the subscriber's dietary and nutritional intake and eating practices over time. For example, data may be obtained by periodically requesting information on what, how much, and when the subscriber ate and/or drank. The requests for information may target the time period of about 2 to about 8 hours preceding the request and the requests may be systematically timed so that every conscious hour may be eventually subjected to multiple requests for information. Next, the subscriber's food intake (including drinks and snacks) may be subjected to a comprehensive nutritional evaluation which establishes the nutritional value of the ingested substances including the amount and type of vitamins, minerals, calories, protein, carbohydrates, antioxidants, sodium, fats and the like. Each meal and snack (including drinks) is assessed and registered in order to construct a detailed, chronological image of the subscriber's dietary intake. This data may be subjected to pattern-analysis in order to identify repetitive patterns and associate fluctuations within the patterns to their influencing factors. The resulting diet and nutritional profile may be continuously updated in order to represent the subscriber's most current dietary intake. As an additional feature, specific food and drink descriptions and quantities consumed are documented and used to identify dietary preferences and predispositions.

The environmental exposure data consists of those environmental characteristics that describe both natural environmental considerations (i.e., natural occurrences such as outside air temperature, humidity, sunlight, naturally occurring toxic/hazardous emissions, terrain, rain, water temperature, and others), manmade or man influenced environments considerations (i.e., air conditioning, heating, ergonomics, lighting, pollution and contamination, traffic, and the like), and hazardous environments (i.e., intentional and unintentional manmade or man caused environmental considerations such as exposure to dangerous situations and dangerous substances such as nuclear materials, toxic or hazardous biological substances, and toxic or hazardous chemicals, and the like).

The behavior data (also referred to as behavior profile) documents a variety of behaviors that are known to affect wellness and longevity. To simplify behavior assessment, and, as used herein, "behaviors" are strictly defined as the actions taken by a person to relax, deal with stress, and occupy free time. The behaviors, amount of time spent in these behaviors, and the degree or intensity in which the subscriber participates in a behavior may be registered. The behaviors may be divided into three general categories. The first category includes behaviors that involve taking a substance (alcohol, tobacco, drugs, food, coffee, and the like). The second category includes behaviors that require doing something (jogging, watching sports, gambling, watching TV, playing golf, conversations, sewing, and the like). The third category addresses coping impulses which include impulsive reactions to anger, affection, fear, confusion, and embarrassment. The data acquired may be subjected to a pattern-analysis to identify repetitive patterns and tendencies.

Psychological characteristics address the subscriber's mental state and processes including emotions and behaviors. The physiological characteristics data address the normal and abnormal performance characteristics of the subscriber's organ systems. These may include data such as vital signs, cardiovascular system, respiratory system, nervous system, skin system, musculoskeletal system, blood system, digestive system, endocrine system, urinary system, reproductive system and combinations comprising at least one of the foregoing for establishing unique characteristics and performance that may include visual acuity, blood pressure, heart rate and rhythm, respiratory rate, blood oxygen level, cholesterol levels, estrogen level, hearing acuity and sensitivity, sensory perception, PSA level, insulin levels, mental clarity, responsiveness, gait, posture, balance, teeth and gum condition, skin abnormalities, inflammation, pain, discomfort, discharges and the like.

The medical history of the subject or the response the subject gives to in response to the one or more questions about the subject's medical history may be used in the determination of the subject's mental status by virtue of the symptoms or symptoms groups displayed by subjects. Without limiting the scope of the present disclosure, exemplary symptoms are somatic concern, anxiety, depressed mood, suicidality, guilt, hostility, aggression, elated mood, grandiosity, pressure of speech, suspiciousness/persecution, auditory or visual hallucinations, ideas of reference or control, unusual or bizarre thought content, thought disorder, bizarre behavior, self-neglect, self-harm, threats to others, disorientation, conceptual disorganization, blunted or flat affect, emotional withdrawal, apathy, social withdrawal, social anxiety, motor retardation, tension, uncooperativeness, excitement, inattention, distractibility, motor hyperactivity, mannerisms or posturing, movement disorder, delusions, poor rapport, passivity, poor abstract thinking, reduced or absent theory of mind, reduced insight, reduced judgment, reduced memory, anti-social traits, tendencies or acts, chronic regional pain or other unexplained chronic pain syndrome, offending behavior of a forensic nature, disturbance of volition, poor impulse control, anger, delayed gratification difficulty, affective lability, mood lability, mood swings, active social avoidance, preoccupation, obsessional preoccupation, ruminations, disturbance of spontaneity or flow of conversation, poor self care, anxious worrying, tension, tonicity, grasp strength, rumination, fear, active/intentional and passive/unintentional avoidance, dissociation, stress, attenuated psychotic symptoms, overvalued ideation, brief intermittent psychotic symptoms, subjective self-disturbance, re-experiencing phenomena, sense of presence, distancing, corporeality, disturbed stream of consciousness, self-other boundary disturbances, self-demarcation disturbances, body image disturbances, anorexia, orientation and re-orientation disturbances, self-consciousness, first rank passivity symptoms, ideas of reference or control, loss of sense of self, thought insertion, thought broadcasting, thought blocking, thought replacement, abnormal perception, delusional attribution or interpretation, under-arousal, disinhibition, impulsivity, over-aropusal, difficulty attending, reduced attention span, scattered attention, distressing recollections, emotional dysregulation, implausible belief, obsessional compensations, intrusive auditory thoughts, euphoria, apathy, and irritability.

In some embodiments, the at least one attribute includes characteristics of certain receptors, such as serotonin receptors, dopamine receptors, estrogen receptors and adrenergic receptors in the subject. In some embodiments, at least one attribute includes the one or more events, such as stroke, hypertension, diabetes, cardiovascular diseases, kidney disorders can cancer, in the subject's medical history.

In some embodiments, the method of determining the mental state of a subject comprises determining the mental competency to perform a function. In certain embodiments, the function concerns the capacity to operate a firearm. In other embodiments, the function comprises operating a motor vehicle. In some embodiments, the motor vehicle is an automobile. In other embodiments, the motor vehicle is an aircraft, boat or ship.

In some embodiments, the method comprises determining the mental state of a subject in order to determine whether the subject can purchase and/or possess a firearm, whether the subject possesses the mental capacity to safely operate a firearm, whether the subject has the mental capacity to safely own or operate a motor vehicle, or whether the subject's responses are contrary to other information previously supplied to other health professionals, law enforcement professionals, probation officials, immigration authorities or other governmental agencies.

In some embodiments, the mental state of the subject is determined based on the assessment score. In further embodiments, a depression severity questionnaire is presented to the subject when the score indicates the presence of depression in the subject. In other embodiments, the method further comprises collecting demographic information regarding the subject. This information may be used in the calculation of one or more of the assessment scores.

The system may further include an alert database, which includes information concerning a number of mental states or behavioral disorders that can pose a danger to the subject, the subject's family, other people, as well as property. In certain cases, the alert may be related to a health danger such as, but not limited to, heart attack, stroke, aneurism, or dementia. In other cases, the alert is related to the capacity to own or operate firearms or motor vehicles. In other cases, the alert may relate to information contrary to information previously supplied by the subject to government authorities or agencies.

In some embodiments, the alert database includes a matrix for converting one or more responses to one or more questions in the assessment to generate one of more assessment scores for determining if the system should additionally send an automatic alert to one or more additional health professionals, law enforcement professionals, probation officials, motor vehicle licensing professionals, immigration officials, or a combination thereof. Each of assessment scores may be compared with a threshold score for activating the alert, wherein a score exceeding the threshold triggers activation of the alert. In some embodiments, the alert is categorized into multiple levels e.g., level 1, level 2 and level 3 alert with level 3 alert being the most serious alert level. In some embodiments, the alert level is color-coded, e.g., level blue, level orange and level red alert with level red alert being the most serious alert level. In some embodiments, the alert is presented in the form of an alert signal on the computer screen for the health professionals' review. In other embodiments, the alert level is listed as an item of an assessment report generated by the system for review by the health professionals.

In some embodiments, the at least one attribute from the medical history and/or the at least one response to the one or more questions about the medical history triggers the system to present an automatic alert for review by the at least one health professional if the at least one attribute from the medical history and/or the at least one response to the one or more questions about the medical history matches an alert event in the alert database.

Pursuant to the review by the health professional and an analysis of other alert events in the alert database, the system may further send an automatic alert to additional health professionals, law enforcement professionals, probation officials, motor vehicle licensing professionals, immigration authorities, or a combination thereof.

In yet other embodiments, there are a plurality of assessments; and the plurality of assessments are administered preferentially. In some embodiments, the term "administered preferentially" means that a subsequent assessment is administered to the subject based upon an answer to a preceding assessment.

In even other embodiments, the system is configured on a handheld device. In some embodiments the handheld device is a laptop computer, tablet computer, smartphone, or PDA.

In some embodiments, the method further comprises determining if the subject is undergoing an initial wellness assessment or a follow-up.

The determined mental state can include any of the above-described disorders. In certain embodiments, the determined mental state is a behavioral disorder selected from the group consisting of depression, substance abuse, risk for bipolar disorder, and post-traumatic stress disorder.

System for Assessment of a Mental State of a Human Subject

Another aspect of the present application relates to a system for assessment of a mental state of a subject. The system includes: a computer-readable memory, the computer-readable memory configured to store computer-executable instructions; an input device configured to receive an input from the subject; and a processor configured to execute the computer-executable instructions. The computer-executable instructions include prompting the subject with at least one question in a system for assessment of mental state on a display; recording at least one response to the at least one assessment, wherein the at least one response comprises a long-form answer; converting the at least one response into at least one assessment score; generating an output comprising the at least one assessment score for assessment of the mental state of the subject by at least one health professional; retrieving a medical history of the subject from a database and accepting at least one attribute from the medical history for the determination of the mental state of the subject, and/or presenting one or more questions about the medical history of the subject and receiving at least one response to the one or more questions about the medical history of the subject for the determination of the mental state of the subject, wherein the at least one attribute from the medical history and/or the at least one response to the one or more questions about the medical history triggers the system to present an automatic alert for review by the at least one health professional if the at least one attribute from the medical history and/or the at least one response to the one or more questions about the medical history matches an alert event in an alert database; and generating a report of the mental state of the subject based on the assessment by the at least one health professional and incorporating the report into an electronic health record associated with the subject.

In some embodiments, the computer-executable instructions further comprise: a plurality of assessments; and the plurality of assessments is administered preferentially.

In some embodiments, the system is configured on a handheld device.

In other embodiments, the computer-executable instructions further comprise determining if the subject is undergoing an initial wellness assessment or a follow-up.

In yet other embodiments, the computer-executable instructions further comprise collecting demographic information regarding the subject.

In certain embodiments, the diagnosed behavior disorder includes, or is caused by, a mental disorder or a behavioral disorder as described herein. In particular embodiments, the diagnosed behavioral disorders include at least one of depression, substance abuse, risk for bipolar disorder, and post-traumatic stress disorder.

FIG. 1 is a block diagram illustrating exemplary hardware components that may be used for implementing aspects of the system and method for using a wellness assessment behavioral health kiosk 10. A computer system 100 may include and execute programs to perform functions described herein, including steps of method described above. While only one processor 114 is shown in FIG. 1, it is understood that the computer system 100 used to implement the wellness assessment behavioral health kiosk 10 may include multiple processors. Additionally, a system for implementing the wellness assessment behavioral health kiosk 10 may include multiple networked computer systems 100. Further, a mobile device that includes some of the same components of computer system 100 may perform steps of the method described above. Computer system 100 may connect with a network 118, e.g., Internet, or other network, to receive inquires, obtain data, and transmit information (e.g., to a user work station or other user computing device) as described above.

Computer system 100 typically includes a memory 102, a secondary storage device 112, and a processor 114. Computer system 100 may also include a plurality of processors 114 and be configured as a plurality of, e.g., bladed servers, or other known server configurations. Computer system 100 may also include an input device 116, a display device 110, and an output device 108.

Memory 102 may include RAM or similar types of memory, and it may store one or more applications for execution by processor 114. Secondary storage device 112 may include a hard disk drive, floppy disk drive, CD-ROM drive, or other types of non-volatile data storage. Processor 114 may include multiple processors or include one or more multi-core processors. Any type of processor 114 capable of performing the calculations described herein may be used. Processor 114 may execute the application(s) that are stored in memory 102 or secondary storage 112, or received from the Internet or other network 118. The processing by processor 114 may be implemented in software, such as software modules, for execution by computers or other machines. These applications preferably include instructions executable to perform the functions and methods described above and illustrated in the Figures herein. The applications may provide graphic user interfaces (GUIs) through which users may view and interact with the application(s).

Also, as noted, processor 114 may execute one or more software applications in order to provide the functions described in this specification, specifically to execute and perform the steps and functions in the methods described above. Such methods and the processing may be implemented in software, such as software modules, for execution by computers or other machines.

Input device 116 may include any device for entering information into computer system 100, such as a touch-screen, keyboard, mouse, cursor-control device, microphone, digital camera, video recorder or camcorder. Input device 116 may be used to enter information into GUIs during performance of the methods described above. Display device 110 may include any type of device for presenting visual information such as, for example, a computer monitor or flat-screen display (or mobile device screen). Output device 108 may include any type of device for presenting a hard copy of information, such as a printer, and other types of output devices include speakers or any device for providing information in audio form.

Examples of computer system 100 include dedicated server computers, such as bladed servers, personal computers, laptop computers, notebook computers, palm top computers, network computers, mobile devices, or any processor-controlled device capable of executing a web browser or other type of application for interacting with the system. If computer system 100 is a server, server 100 may not include input device 116, display device 110 and output device 108. Rather, server 100 may be connected, e.g., through a network connection to a stand-alone work station (another computer system) that has such devices.

Although only one computer system 100 is shown in detail, the system for using a wellness assessment behavioral health kiosk 10 may use multiple computer systems or servers as necessary or desired to support the users, as described above. Aspects may also use back-up or redundant servers to prevent network downtime in the event of a failure of a particular server. In addition, although computer system 100 is depicted with various components, one skilled in the art will appreciate that the server can contain additional or different components. In addition, although aspects of an implementation consistent with the above are described as being stored in memory, one skilled in the art will appreciate that these aspects can also be stored on or read from other types of computer program products or computer-readable media, such as secondary storage devices, including hard disks, floppy disks, or CD-ROM; or other forms of RAM or ROM. Computer-readable media may include instructions for controlling a computer system, such as the computer system 100, to perform a particular method, such as methods described above.

Figure 2A:
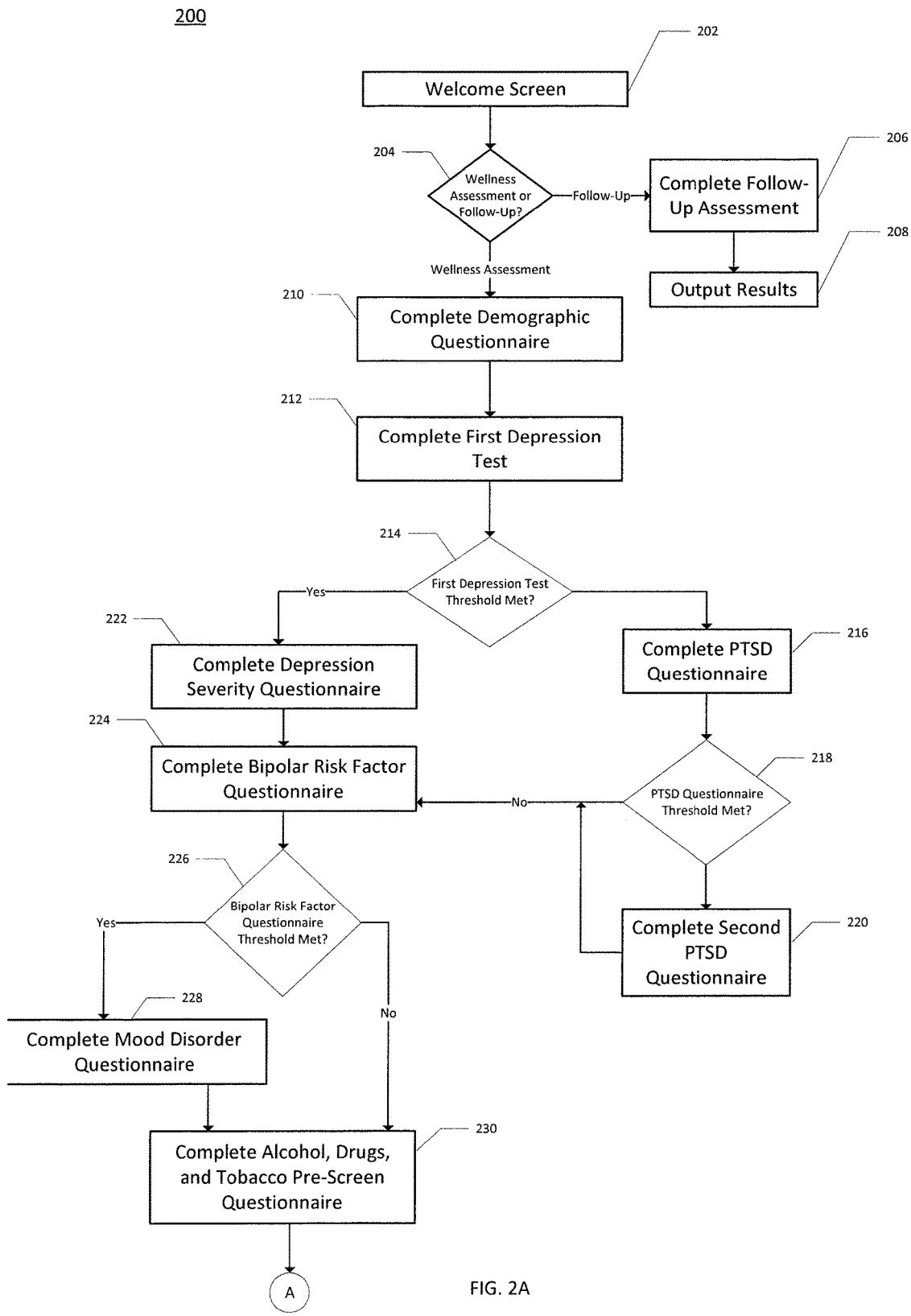
FIGS. 2A and 2B show an exemplary method of using the wellness assessment behavioral health kiosk.
Figure 2B:
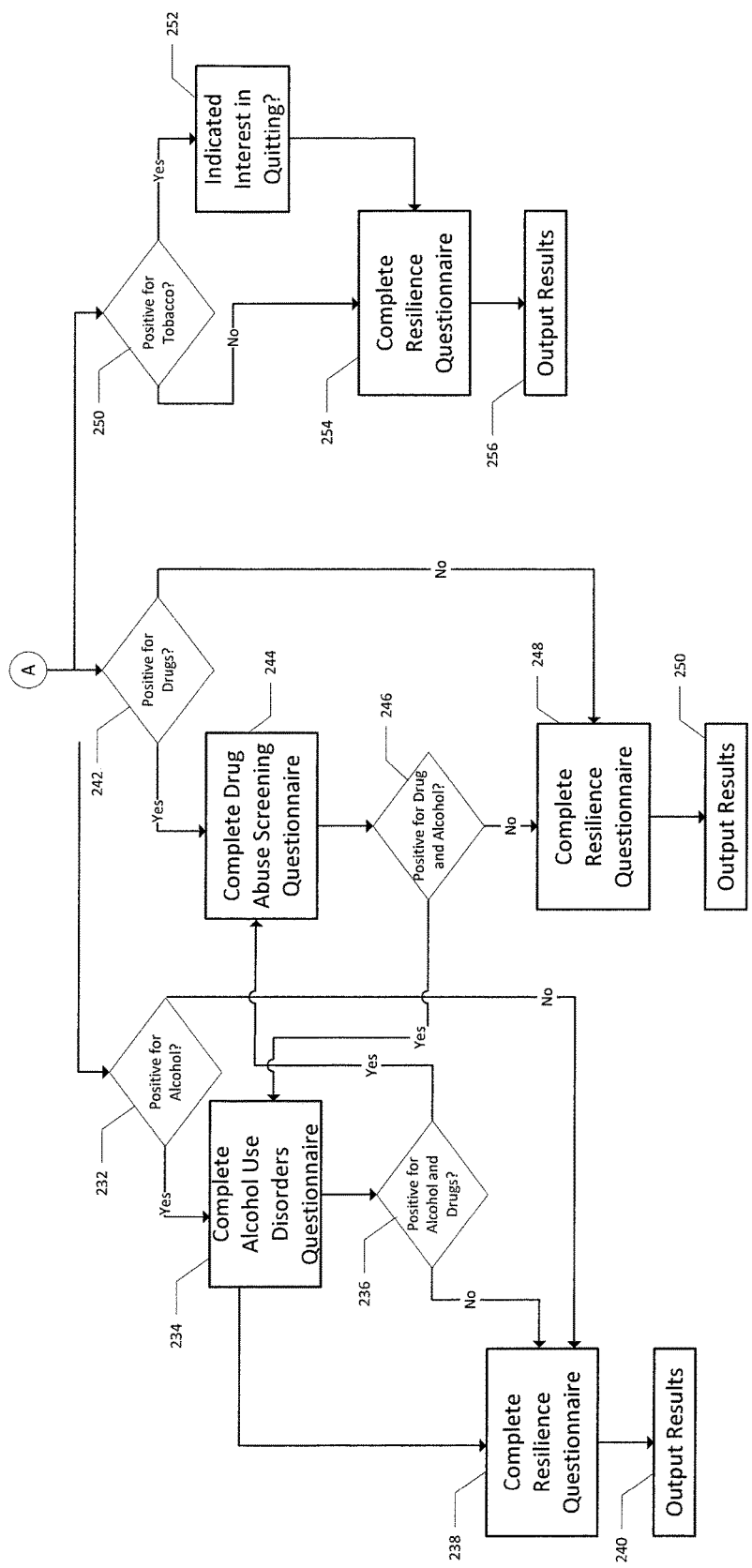

FIGS. 2A and 2B show a method 200 of using the wellness assessment behavioral health kiosk 10, according to one aspect of this disclosure. The method 200 may begin by providing a welcome screen at block 202 to a user of the wellness assessment behavioral health kiosk 10. At the welcome screen, the wellness assessment behavioral health kiosk 10 may prompt the user to select from, for example, two options. One option may be that the user is conducting her first wellness assessment and therefore, the user completes the full wellness assessment. Alternatively, the user may have already previously conducted a wellness assessment and is at the facility to conduct a follow-up visit. At block 204, the method 200 may determine which option the user has selected. If the user selects the option of a follow-up visit, the method 200 may proceed to block 206. If the user selects conducting an entire wellness assessment, the method 200 may proceed to block 210.

At block 206, the method may prompt the user to complete a follow-up assessment. The follow-up assessment may ask the user a variety of questions related to the user. For example, the follow-up assessment may ask the user questions about the user's progress. These questions may be tailored to the previous wellness assessment the user may have taken. For example, if the user had previously talked to her healthcare professional about an alcohol abuse problem, the method 200 may ask the user follow-up questions related to alcohol abuse. For example, the method 200 may ask the user if the user has decreased the amount of alcohol the user consumes per week or if she has sought additional help, for example, attending Alcoholics Anonymous meetings. These questions may be set without customization to the user. Alternatively, the questions may be tailored to the user based on, for example, notes previously made entered into the wellness kiosk by the user's healthcare professional. Once the user completes the follow-up questionnaire, the method 200 may proceed to block 208.

At block 208, the method 200 may output the results of the follow-up questionnaire completed in block 206. For example, the method 200 may print the questions and answers of the follow-up questionnaire. Alternatively, or additionally, the method 200 may output the results of the follow-up questionnaire electronically. For example, the method 200 may output the results as an email to the user's healthcare professional. Alternatively, or additionally, the method 200 may output the results to the user's electronic health records. For example, the results may be incorporated into the user's preexisting electronic health records. If the user does not have a preexisting electronic health record, then the method may generate a new electronic health record for the user.

If, at block 204, the user selected to start a new wellness assessment, the method 200 may continue to block 210. At block 210, the wellness assessment behavioral health kiosk 10 may prompt the user to enter demographic information. The demographic information may include, for example, the user's age, weight, height, ethnicity, gender, education, household composition, employment status, and other factors that may be useful in diagnosing the user. One of ordinary skill in the art would readily recognize that many other demographic aspects may be useful in diagnosing the user. Once the user has entered the demographic information, the method 200 may proceed to block 212.

At block 212, the wellness assessment behavioral health kiosk 10 may prompt the user to answer a series of behavioral questions. For example, the wellness assessment behavioral health kiosk 10 may ask the user to complete a series of questions related to the frequency of depressed mood and anhedonia over a period of time. For example, one common questionnaire used in diagnosing mental health conditions is the Patient Health Questionnaire-2 (PHQ-2). The PHQ-2 is used generally to screen for depressive behavior rather than a final diagnosis. Using the PHQ-2, the wellness assessment behavioral health kiosk 10 may ask the user about the user's frequency of depressed mood and anhedonia over the past two weeks. Based on the answers to the questions presented by the PHQ-2, the wellness assessment behavioral health kiosk 10 may assign a score to the user. In one aspect of this disclosure, the higher the score the wellness assessment behavioral health kiosk 10 assigns to the user's responses, the more likely that the user may be depressed. When the user has completed the behavioral health questions in block 212, the method 200 may proceed to block 214.

At block 214, the wellness assessment behavioral health kiosk 10 may analyze the score generated in block 212. For example, the wellness assessment behavioral health kiosk 10 may have a minimum threshold for screening for depression. For example, the wellness assessment behavioral health kiosk 10 may determine that the user may have depression if the score is equal to or higher than two. One of ordinary skill in the art would readily recognize that any threshold may be used. For example, the lower the threshold, the more sensitive the wellness assessment behavioral health kiosk 10 may be to detecting depressive behavior. Conversely, the higher the threshold, the less sensitive the wellness assessment behavioral health kiosk 10 may be to detecting depressive behavior. If the threshold in block 214 has not been met, then the method 200 may proceed to block 216. If the threshold in block 214 has been met, then the method 200 may proceed to block 222.

At block 216, the wellness assessment behavioral health kiosk 10 may ask the user to complete a post-traumatic stress disorder (PTSD) questionnaire. For example, the wellness assessment behavioral health kiosk 10 may ask the user questions from the primary care PTSD (PC-PTSD) screen. For example, the PC-PTSD screen may include an introductory sentence or paragraph to cue respondents to traumatic events. The PC-PTSD screen may then ask a series of questions to the user to detect PTSD. Based on the answers to the questions, the wellness assessment behavioral health kiosk 10 may generate a score. Once the user has completed the PTSD questionnaire in block 216, the method 200 may proceed to block 218.

At block 218, the wellness assessment behavioral health kiosk 10 may analyze the generated PTSD questionnaire score to determine the likelihood that the user suffers from PTSD. For example, the wellness assessment behavioral health kiosk 10 may have a minimum threshold for screening for PTSD. For example, the wellness assessment behavioral health kiosk 10 may determine that the user may have PTSD if the score is equal to or higher than three. One of ordinary skill in the art would readily recognize that any threshold may be used. For example, the lower the threshold, the more sensitive the wellness assessment behavioral health kiosk 10 may be to detecting PTSD. Conversely, the higher the threshold, the less sensitive the wellness assessment behavioral health kiosk 10 may be to detecting PTSD. If the threshold in block 218 has not been met, then the method 200 may proceed to block 224. If the threshold in block 218 has been met, then the method 200 may proceed to block 220.

At block 220, the wellness assessment behavioral health kiosk 10 may ask the user to complete a second PTSD questionnaire. This second PTSD questionnaire may ask questions in more depth than the PTSD questionnaire in block 216. For example, the wellness assessment behavioral health kiosk 10 may ask questions that are found in the PTSD CheckList—Civilian Version. The wellness assessment behavioral health kiosk 10 may generate a score based on the answers the user provided to the questions. Once the user has completed the second PTSD questionnaire, the method 200 may proceed to block 224.

If the user did meet the threshold in block 214, the method 200 may proceed to block 222. At block 222, the wellness assessment behavioral health kiosk 10 may ask the user to complete a more in-depth depression severity questionnaire. For example, the wellness assessment behavioral health kiosk 10 may ask the user to complete a Patient Health Questionnaire-9 (PHQ-9). The PHQ-9 may be used to screen, diagnose, monitor, and measure a severity of depression. The more in-depth depression severity questionnaire of block 222 may be a continuation of the questionnaire presented in block 212. Based on the answers provided by the user, the wellness assessment behavioral health kiosk 10 may generate a score that represents, for example, whether the user exhibits depressive behavior and the severity of any depressive behavior. After block 222 is complete, the method 200 may proceed to block 224.

At block 224, the wellness assessment behavioral health kiosk 10 may ask the user to complete a bipolar risk factor questionnaire. For example, the wellness assessment behavioral health kiosk 10 may ask the user if the user had ever been diagnosed with bipolar disorder or had ever experienced a manic episode. Additionally, or alternatively, the wellness assessment behavioral health kiosk 10 may ask the user about the user's family history. For example, the wellness assessment behavioral health kiosk 10 may ask if any of the user's parents, siblings, or other ancestors had suffered from bipolar disorder or had ever experienced a manic episode. Additionally, or alternatively, the wellness assessment behavioral health kiosk 10 may ask the user for additional details regarding the subject's depression. For example, the wellness assessment behavioral health kiosk 10 may prompt the user for information, such as how suddenly the depression symptoms manifested. Additionally, or alternatively, the wellness assessment behavioral health kiosk 10 may ask the user when the first depressive episode occurred. For example, the wellness assessment behavioral health kiosk may ask the user if the first depressive episode occurred before a certain age, such as eighteen years old. Once the user has answered these questions, the wellness assessment behavioral health kiosk 10 may generate a score based on the answers provided by the user. After block 224 is complete, the method 200 may proceed to block 226.

At block 226, the wellness assessment behavioral health kiosk 10 may determine, based on the score generated in block 224, whether the user should be further screened for a mood disorder. For example, the wellness assessment behavioral health kiosk 10 may have a minimum threshold for screening for bipolar disorder risk. For example, the wellness assessment behavioral health kiosk 10 may determine that the user may have bipolar disorder if the score is equal to or higher than one. One of ordinary skill in the art would readily recognize that any threshold may be used. For example, the lower the threshold, the more sensitive the wellness assessment behavioral health kiosk 10 may be to detecting bipolar disorder. Conversely, the higher the threshold, the less sensitive the wellness assessment behavioral health kiosk 10 may be to detecting bipolar disorder. If the threshold in block 226 has not been met, then the method 200 may proceed to block 230. If the threshold in block 226 has been met, then the method 200 may proceed to block 228.

At block 228, the wellness assessment behavioral kiosk 100 may ask the user additional questions related to the user's mood. After the user has answered the questions, the wellness assessment behavioral kiosk 100 may generate a score based on the answers. When block 228 is finished, the method 200 may proceed to block 230.

At block 230, the wellness assessment behavioral kiosk 100 may ask the user pre-screening questions related to alcohol, drug, and tobacco use. For example, the wellness assessment behavioral kiosk 100 may use the Screening, Brief Intervention, and Referral to Treatment (SBIRT) pre-screening questions. For example, the SBIRT pre-screen may ask when the user last had a certain amount of drinks in a given period of time, such as four drinks in one day. Additionally, or alternatively, the SBIRT pre-screen may ask the user if the user has used drugs within a period of time, such as within the last twelve months. Additionally, or alternatively, the SBIRT pre-screen may ask the user if the user uses tobacco in any form. Once the user has answered these questions, the wellness assessment behavioral kiosk 100 may store the answers. The stored answers may be used later in the method 200, as described below. Once block 230 is complete, the method proceeds along path A, which continues on to FIG. 2B. Path A may branch into three different directions. For example, path A may continue to block 232.

At block 232, the wellness assessment behavioral kiosk 100 may determine if the user has answered positively to alcohol. In other words, block 232 may determine if the user has used alcohol as described above with reference to block 230. If the user is not positive for alcohol, then the method 200 may proceed to block 238. However, if the user is positive for alcohol, then the method 200 may proceed to block 234.

At block 234, the wellness assessment behavioral kiosk 100 may ask the user to complete an alcohol use disorders questionnaire. For example, the alcohol use disorders questionnaire may be the Alcohol Use Disorders Identification Test (AUDIT). In one aspect, the wellness assessment behavioral kiosk 100 may use AUDIT to ask the user ten questions to gauge the user's alcohol consumption, drinking behaviors, and alcohol-related problems. Such questions may include questions regarding the frequency of alcohol use, the type of alcohol used, and whether the alcohol use has impaired the user's ability to function in day to day life. The wellness assessment behavioral kiosk may generate a score based on the answers the user provided in response to the alcohol use disorders questionnaire. Once the user has finished answering the questionnaire, the method 200 may proceed in two parallel paths. For example, in one of the parallel paths, the method 200 may proceed to block 238. In the other parallel path, the method 200 may proceed to block 236, which is analyzed in the context of both alcohol and drugs.

At block 238, the wellness assessment behavioral health kiosk 10 may ask the user to complete a set of resilience questions. Once the user has answered the resilience questions, the method 200 may proceed to block 240.

At block 240, the wellness assessment behavioral health kiosk 10 may output the results of the wellness assessment. For example, the method 200 may print the questions and answers of the assessment. Alternatively, or additionally, the method 200 may output the results of the assessment electronically. For example, the method 200 may output the results as an email to the user's healthcare professional. Alternatively, or additionally, the method 200 may output the results to the user's electronic health records. For example, the results may be incorporated into the user's preexisting electronic health records. If the user does not have a preexisting electronic health record, then the method may generate a new electronic health record for the user. The method 200 may then end.

Another parallel path the method 200 may have taken after block 230 is block 242, which determines if the user has answered positively for drugs. If the user has answered positively for drugs, the method 200 may proceed to block 244.

At block 244, the wellness assessment behavioral kiosk 100 may ask the user to complete a drug abuse screening questionnaire. In one aspect, the drug abuse screening questionnaire may be the Drug Abuse Screening Test (DAST). The DAST may ask, for example, ten questions about the user's drug use in the past twelve months. The DAST asks only about drug use, not alcohol or tobacco. One of ordinary skill in the art would readily recognize that tests other than DAST may be used and that these other tests may ask questions about other behavior, including alcohol and tobacco use. For example, the wellness assessment behavioral health kiosk may ask the user for what types of drugs the user uses, the frequency of use for each type of drug, the form in which the user uses the drug, and other questions designed to explore the user's drug use behavior. Once the user has completed the drug abuse screening questionnaire, the method 200 may proceed to block 246.

At block 246, the wellness assessment behavioral kiosk 100 may determine if the user has answered positively for both alcohol and drug use. If the user has answered positively for both alcohol and drug use, the method 200 may proceed to block 234, as described above. However, if the user has not answered positively for both drugs and alcohol, the method 200 may proceed to block 248.

At block 248, the wellness assessment behavioral kiosk 100 may ask the user to complete a set of resilience questions. These resilience questions may be the same as or similar to the resilience questions asked in block 238, as described above. Once the user has completed block 248, the method 200 may proceed to block 250.

At block 250, the wellness assessment behavioral kiosk 100 may output the results of the wellness assessment. Block 250 is similar to block 240, as described above.

If the user did not answer positively for drugs at block 242, the method 200 may proceed directly to block 248 and then to block 250, as described above.

Another parallel path method 200 may take after block 230 is block 252, which determines if the user has answered positively for tobacco use. If the user has indicated that the user uses tobacco, then the method 200 may proceed to block 254.

At block 254, the method 200 may ask the user if the user is interested in quitting tobacco use. Once the user completes this block 254, the method 200 may proceed to block 256.

At block 256, the wellness assessment behavioral kiosk 100 may ask the user a series of resilience questions. These questions may be identical or similar to the resilience questions asked in blocks 238 and 248. Once block 256 is completed, the method 200 may proceed to block 258.

At block 258, the wellness assessment behavioral kiosk 100 may output the results of the wellness assessment. The wellness assessment behavioral kiosk 100 may output the results as described above in, for example, blocks 240 and 250. However, if the user was not positive for tobacco at block 252, then the method 200 may proceed directly to blocks 256 and then 258, as described above. The method 200 may then end.

At each block of the method 200, the wellness assessment behavioral kiosk 100 may allow the user to input additional information. For example, for a given questionnaire, the questionnaire may allow the user to input sentences, short answers, or paragraphs to elaborate on the answers already given. In this way, the user is able to provide a more comprehensive answer that may provide nuance lost in the questionnaire.

Additionally, in another aspect of this disclosure, healthcare professionals may be able to specify certain important words or phrases in any of the longer responses provided by the user. For example, if the user provides, in a long for answer, that the user is contemplating suicide by using the word suicide, the wellness assessment behavioral kiosk 100 may be configured to highlight the word suicide in the outputted results. These important words or phrases may be generally applicable to all users of the wellness assessment behavioral kiosk 100. Additionally, or alternately, the important words or phrases may be tailored for each user, based on previously provided answers or course of treatment. In this way, the healthcare professional may be quickly alerted to areas of particular concern.

Moreover, as described in the description of the method 200, various blocks may generate a score based on the responses given by the user. The method 200 may then compare the generated score to various score thresholds. In one aspect of this disclosure, a score threshold may be pre-defined and unchangeable. In another aspect of this disclosure, the score threshold may be configurable by, for example, a healthcare professional. Moreover, in another aspect of this disclosure, the score threshold may be tailored for each user. For example, if a user has shown in the past to be more vulnerable to alcohol abuse, the score threshold may be lower for this user to attempt to prevent the alcohol abuse from becoming worse. Moreover, in another aspect, the score threshold may be dependent on demographic information. For example, if a user indicates that the user is divorced, the score threshold for that user for depressive behavior may be reduced.

Figure 3:
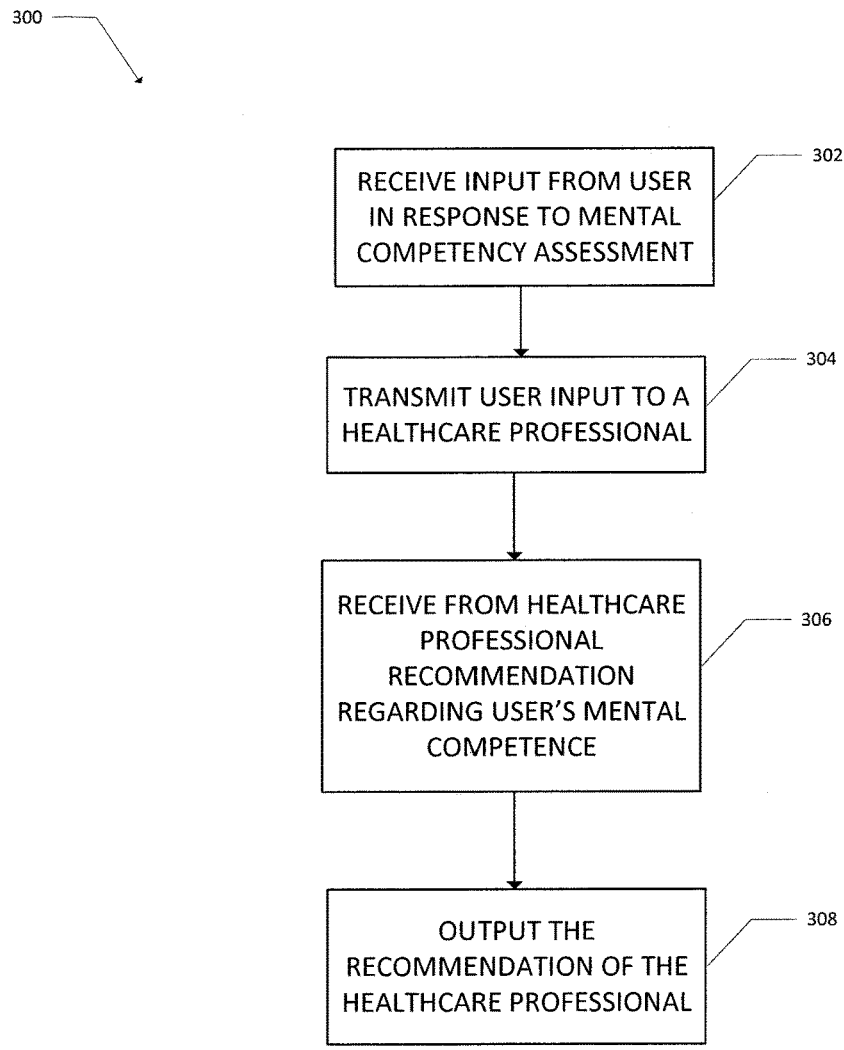
FIG. 3 shows another exemplary method of using the wellness assessment behavioral health kiosk.

FIG. 3 shows another exemplary method 300 of using the wellness assessment behavioral health kiosk 10. The method 300 may begin at block 302. At block 302, the wellness assessment behavioral health kiosk 10 may receive input from a user in response to a mental competency assessment. For example, the wellness assessment behavioral health kiosk 10 may receive input from the user in response to various assessments, such as the assessments described above, for example, in blocks 204, 206, 210, 212, 216, 220, 222, 224, 228, 230, 234, 238, 244, 248, 252, and 254 in method 200. After block 302 is complete, the method 300 may proceed to block 304.

At block 304, the wellness assessment behavioral health kiosk 10 may transmit the user input gathered in block 302 to a healthcare professional. While FIG. 3 shows that block 304 follows block 302, one of ordinary skill in the art would readily recognize that the wellness assessment behavioral health kiosk 10 may transmit the inputted information as the user inputs the information or it may transmit the inputted information once all of the information has been gathered. The user input may be transmitted to another device, such as a computer located near a healthcare professional. One of ordinary skill in the art would readily recognize that any device capable of receiving such information may receive the transmitted information. The user input may be transmitted over a network, such as network 118. The healthcare professional may be, for example, a primary physician. There may also be more than one healthcare professional. For example, the information may be transmitted to multiple healthcare professionals who may analyze the information jointly. Based on the analysis, the one or more healthcare professionals may generate a recommendation based on the transmitted information. The recommendation may include the mental competency of the user. The recommendation may also include a treatment plan. After block 304 is complete, the method 300 may proceed to block 306.

At block 306, the wellness assessment behavioral health kiosk 10 may receive the recommendation generated in block 304. The recommendation generated in block 304 may be transmitted to the wellness assessment behavioral health kiosk 10 using, for example, a computer located near the healthcare professional. One of ordinary skill in the art would readily recognize that any device capable of transmitting such information may transmit the recommendation. The recommendation may be transmitted over a network, such as network 118. After block 306 is completed, the method 300 may continue to block 308.

At block 308, the wellness assessment behavioral health kiosk 10 may output the recommendation received in block 306. The output may presented to the user who input information into the wellness assessment behavioral health kiosk 10. Alternatively, or additionally, the output may be presented to a third party. As described above, the outputted recommendation may include a course of treatment. After block 308 is complete, the method 300 may end.

Method for Treating a Behavioral Disorder

Another aspect of the present application relates to a method for treating a behavioral disorder in a subject in need thereof. The method includes the steps of: prompting the subject with at least one question on a display of a system for assessment of a behavioral disorder of the subject, wherein the system comprises the display, an input device, a processor and a database; recording at least one response to the system, wherein the at least one response comprises a long-form answer; analyzing the at least one response by at least one health professional; determining by the at least one health professional, based on the at least one response, the behavioral disorder of the subject; and incorporating the behavioral disorder of the subject into an electronic health record associated with the subject. The method further comprises administering to the subject at least one treatment effective for the behavioral disorder.

In some embodiments, the method further comprises the step of retrieving a medical history of the subject from a database and accepting the at least one attribute from the medical history for the determination of the behavioral disorder of the subject. In some embodiments, the method further comprises the step of presenting one or more questions about the medical history of the subject and receiving responses to the one or more questions about the medical history of the subject for the determination of the behavioral disorder of the subject.

In some embodiments, the at least one attribute from the medical history and/or the at least one response to the one or more questions about the medical history triggers an automatic alert for review by the at least one health professional if the at least one attribute from the medical history and/or the at least one response to the one or more questions about the medical history matches an alert event in an alert database.

In some embodiments, the method comprises analyzing the at least one response by two health professionals. In some further embodiments, the at least one health professional is a mental health professional. In still further embodiments, the mental health professional is a psychiatrist. In other further embodiments, the at least one health professional is a physician. In yet other embodiments, the two health professionals are a physician and a mental health professional.

In particular embodiments, the method further comprises the step of converting the at least one response into an assessment score based on a matrix.

There are numerous art-known therapeutic regimes for the treatment of behavioral disorders. In certain embodiments, the therapeutic regimes can include treatment with pharmacological compounds that modulate the brain's serotonin and/or norepinephrine systems. Such pharmacological compounds include, but are not limited to, tricyclic antidepressants, selective serotonin reuptake inhibitors (SSRI), selective norepinephrine reuptake inhibitors (SNRI), and serotonin antagonist and reuptake inhibitors (SARI). Specific exemplary pharmacological compounds include amitriptyline (ELAVIL™), clomipramine (ANAFRANIL™), desipramine (NORPRAMIN™), doxepin (SINEQUANT™), imipramine (TOFRANIL™), nortriptyline (PAMELORT™), protriptyline (VIVACTIL™), fluoxetine (PROZAC™), fluvoxamine (LUVOX™), paroxetine (PAXIL™), sertraline (ZOLOFT™), citalopram (CELEXA™), escitalopram oxalate (LEXAPRO™) duloxetine (CYMBALTA™) venlafaxine (EFFEXOR™), mirtazapine (REMERON™), nefazodone (SERZONE™), and desyrel (TRAZODONET™). The foregoing pharmacological compounds can be used singly or in any combination. The foregoing list of exemplary compounds is not exhaustive of those known in the art, which can be used in accordance with the present application.

Non-pharmacological therapeutic regimes include, for example, psychotherapy, including exposure-based psychotherapy, cognitive psychotherapy, and psycho-dynamically oriented psychotherapy; electroconvulsive therapy (ECT).

The above description is for the purpose of teaching the person of ordinary skill in the art how to practice the object of the present application, and it is not intended to detail all those obvious modifications and variations of it which will become apparent to the skilled worker upon reading the description. It is intended, however, that all such obvious modifications and variations be included within the scope of the present application, which is defined by the following claims. The aspects and embodiments are intended to cover the components and steps in any sequence which is effective to meet the objectives there intended, unless the context specifically indicates the contrary.

What is claimed is:

1. A method for generating a medical alert in response to an assessment of a mental state of a human subject, the method comprising:

retrieving a medical history of the subject from a medical histories database and accepting at least one attribute from the medical history for determination of the mental state of the subject, wherein the at least one attribute is obtained by inquiries to the subject and by measurements preformed on the subject, presenting one or more questions to the subject about the at least one attribute from the medical history of the subject, wherein the subject is prompted with at least one question on a display of a graphic user interface of a system for assessment of the mental state of the subject, the system comprising the display, an input device, a processor, a computer-readable memory, the medical histories database, an alert database comprising a plurality of alert events, and a matrix for calculating an assessment score corresponding to the mental state of the subject;

using at least one sensor to perform one or more measurements on the subject comprising at least one of: brain activity, cardiac activity, vascular activity, peripheral neural signals, hemodynamic activity, or metabolic activity, receiving a long form answer to the one or more questions presented to the subject and data acquired by measurements on the subject about the at least one attribute from the medical history of the subject for the determination of the mental state of the subject, recording the long form answer to the one or more questions in the input device of the system, storing at least one response in the memory and determining whether certain pre-specified words or phrases of concern are contained in the long form answer;

programming the processor to:
calculate the assessment score corresponding to the mental state of the subject based on the long form answer and storing the assessment score in the memory, wherein the processor utilizes the matrix to calculate the assessment score based on the long form answer;

compare the one or more measurements on the subject with corresponding one or more predetermined thresholds;

determine by at least one health professional, based on the calculated assessment score and the comparison with the one or more predetermined thresholds, the mental state of the subject; and incorporating the mental state of the subject into an electronic health record associated with the subject that is present in the medical histories database, wherein the assessment score and the comparison with the one or more predetermined thresholds trigger the system to present an automatic alert for review by the at least one health professional if the assessment score matches an alert event in the alert database and the one or more measurements on the subject exceed corresponding one or more predetermined thresholds.

2. The method of claim 1, comprising analyzing the long form answer by two health professionals.

3. The method of claim 2, wherein at least one of the two health professional is a mental health professional.

4. The method of claim 2, wherein at least one of the two health professional is a physician.

5. The method of claim 2, wherein the two health professionals are a physician and a mental health professional.

6. The method of claim 5, wherein the physician is a primary care physician of the subject.

7. The method of claim 1, wherein the determined mental state is a behavioral disorder selected from the group consisting of depression, substance abuse, risk for bipolar disorder, and post-traumatic stress disorder.

8. The method of claim 1, further comprising: collecting demographic information regarding the subject.

9. The method of claim 1, wherein a depression severity questionnaire is presented to the subject when the assessment score indicates the presence of depression in the subject.

* * * * *